United States Patent [19]

Guerineau et al.

[11] Patent Number: 4,745,062

[45] Date of Patent: May 17, 1988

[54] PLASMID VECTORS FOR CLONING AND EXPRESSION OF A PROTEIN IN A MICROORGANISM, COMPRISING AT LEAST ONE PROMOTER FOR EXPRESSION OF β-GLUCOSIDASE IN YEASTS; MICROORGANISMS CONTAINING THESE PLASMIDS; A FERMENTATION PROCESS AND THE ENZYMES OBTAINED

[75] Inventors: Michel M. Guerineau, Paris; Alain Raynal, Gomez Lechatel, both of France

[73] Assignee: Centre National de la Recherche Scientifique, Paris, France

[21] Appl. No.: 678,492

[22] Filed: Dec. 5, 1984

[30] Foreign Application Priority Data

Dec. 6, 1983 [FR] France .................. 83 19494

[51] Int. Cl.[4] .............. C12N 9/42; C12N 15/00; C12N 5/00
[52] U.S. Cl. ................... 435/209; 435/172.3; 435/255; 435/942; 935/14; 935/28; 935/69
[58] Field of Search ............ 435/172.3, 317, 253, 435/255, 68, 70, 209; 935/14, 28

[56] References Cited

U.S. PATENT DOCUMENTS

| | | | |
|---|---|---|---|
| 4,243,752 | 1/1981 | Skinner et al. | 435/209 |
| 4,275,163 | 6/1981 | Gallo | 435/209 |
| 4,464,471 | 8/1984 | Armentrout et al. | 435/253 |
| 4,469,791 | 9/1984 | Colson et al. | 435/253 |
| 4,487,831 | 12/1984 | Day et al. | 435/99 |

FOREIGN PATENT DOCUMENTS 2489363  5/1982  France .

OTHER PUBLICATIONS

Biological Abstracts, vol. 72, No. 8, 1981, p. 5388, No. 51899, Philadelphia, R. W. Armentrout.

Biological Abstracts, RRM, No. 21003547, Philadelphia, S. K. Picataggio.

Primary Examiner—Thomas G. Wiseman
Assistant Examiner—Thomas D. Mays
Attorney, Agent, or Firm—Thomas J. Greer, Jr.

[57] ABSTRACT

The present invention relates to a plasmid vector for cloning and expression of a protein in a microorganism, which comprises at least one structural gene which codes the synthesis of the said protein and elements which ensure the expression of the said structural gene in a microorganism, and wherein the promotion of the structural gene is ensured by the expression promotor of the β-glucosidase gene in yeasts.

The present invention also relates to microorganisms transformed by the said vectors, in particular a transformed strain of S. cerevisiae, a fermentation process using the said vectors, and the enzymes prepared by the said process, in particular β-glucosidase.

4 Claims, 2 Drawing Sheets

B: BamHI, Hp: HpaI, Pv: PvuII, S: SalI

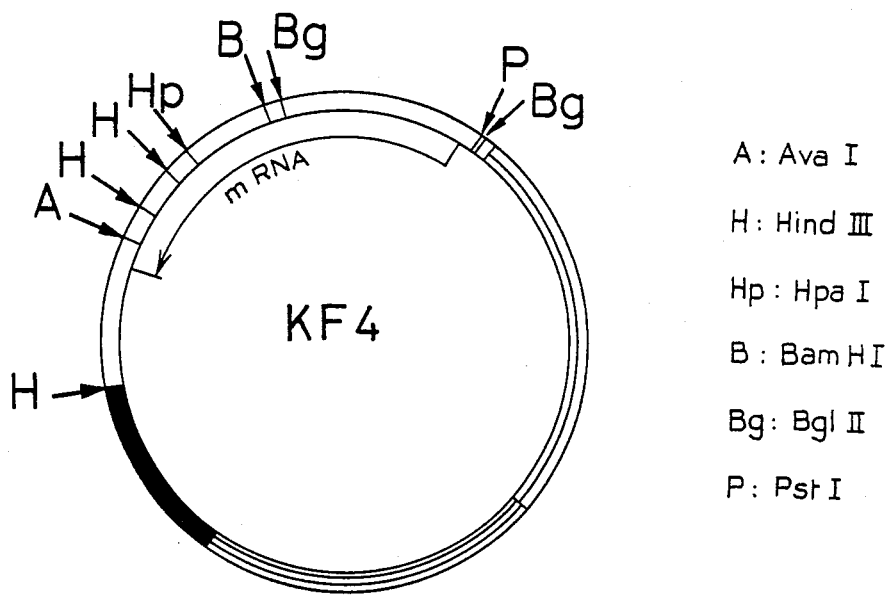
FIG_2
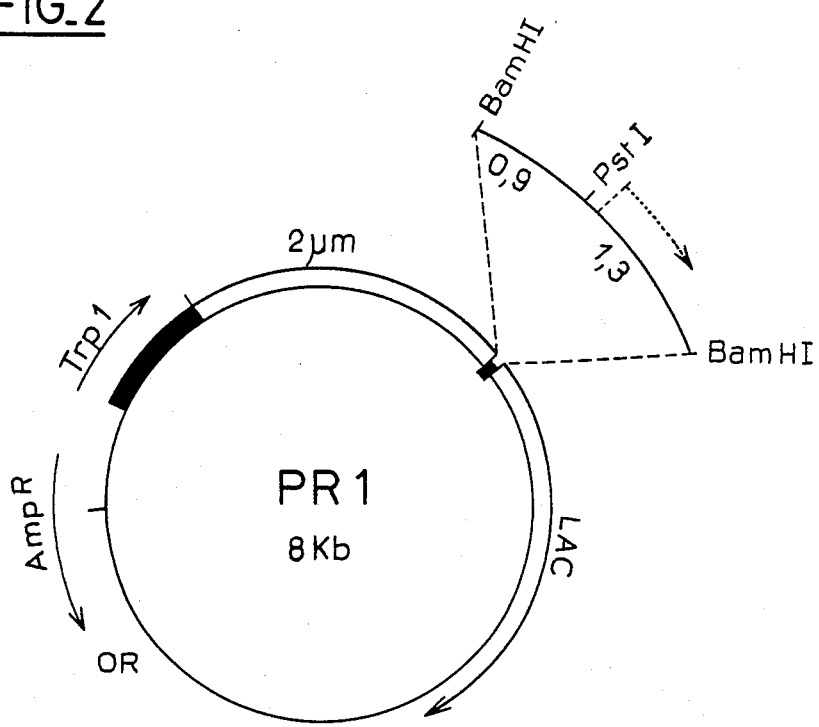
FIG_3

PLASMID VECTORS FOR CLONING AND EXPRESSION OF A PROTEIN IN A MICROORGANISM, COMPRISING AT LEAST ONE PROMOTER FOR EXPRESSION OF β-GLUCOSIDASE IN YEASTS; MICROORGANISMS CONTAINING THESE PLASMIDS; A FERMENTATION PROCESS AND THE ENZYMES OBTAINED

The present invention relates generally to plasmid vectors for cloning and expression of a protein in a microorganism, and in particular in yeasts, the microorganisms transformed by the said plasmid vectors, a fermentation process and the enzymes obtained using the said process.

More particularly, the present invention relates to plasmid vectors for cloning and expression of the gene of β-glucosidase in yeasts, and to its use in enzymatic degradation of cellulose materials.

Degradation of cellulose materials is, in fact, a current economic preoccupation of the first order. Cellulose is one of the chief constituents of wood, cereals and all vegetable substances in general. The valorization of natural and renewable sources which constitute the by-products of sylviculture, agriculture, animal husbandry and the agro-foodstuffs industries, inter alia, by degradation of cellulose into glucose is an important route for the production of energy, but also for the synthesis of products such as: proteins, enzymes, antibiotics and intermediates of organic chemistry (solvents, organic acids).

The recent development of enzyme technology has led to an interest in the enzymatic hydrolysis of cellulose, which could prove to be more economical than the chemical processes used hitherto. It is known that β-glucosidase (EC3-2-1-21) intervenes in the last stage of the degradation of cellulose. It enables the cellobiose to be cleaved into two molecules of glucose.

Numerous bacteria and fungi produce cellulases which are used in industry. However, hydrolysis of cellulose by the cellulose complex results in an accumulation of cellobiose which inhibits the cellulose activity. The rate of hydrolysis of the cellulose could thus be substantially increased by complementing the action of the cellulases by immobilized β-glucosidases. This immobilized enzyme exhibits a high stability. Moreover, it can be reused.

Another interesting procedure would be to dope an organism capable of directly fermenting cellobiose. From this point of view, yeast seems to be an organism of choice. In fact, yeast is grown industrially on inexpensive media for the production of yeast for the panification of beer. It has been consumed by humans for thousands of years, it cannot multiply in humans and it has no pathogenic potency. It is thus a very useful host for genetic recombinations in vitro for the purpose of selection of new industrial strains or the production of enzymes or of proteins, for example.

Cloning of a structural gene of β-glucosidase in *Saccharomyces cerevisiae* has made it possible to obtain transformed *S. cerevisiae* which produce β-glucosidase with a high yield. Study of the structure of the cloned gene has shown that this gene is transcribed starting from a powerful promoter, that is to say that the promoter for expression of the β-glucosidase in yeasts can be used in the high-yield production of proteins—other than β-glucosidase—by fusion between this promoter and the corresponding structural gene or cDNA synthesized from the mature messenger DNA, which is to be cloned.

Another advantage of the present invention is thus the isolation and sub-cloning of the DNA fragment carrying this powerful promoter.

The present invention thus relates to plasmid vectors for cloning and expression of a protein in a microorganism, which comprise at least the structural gene which codes the synthesis of the said protein and elements which ensure expression of the said structural gene in a microorganism, and wherein the promotion of the structural gene is ensured by the promoter for expression of the gene of β-glucosidase in yeasts.

According to one embodiment of the invention, the promoter for expression of the gene of β-glucosidase in yeasts consists of a sequence of chromosomal DNA extracted from a yeast, in particular a strain of *Kluyveromyces fragilis*. It will be, in particular, all or part of the restriction fragment BamH1-BamH1 of 2.2 kb sub-cloned from a plasmid vector according to the invention.

According to another embodiment of the invention, the structural gene of the protein which is to be cloned is, preferably, a eukaryotic gene, in particular the gene which codes the synthesis of β-glucosidase. This gene will originate, in particular, from chromosomal DNA from a strain of *K. fragilis* which produces a β-glucosidase in a constitutive manner and is thus the donor organism.

"Elements which ensure the expression of the structural gene" are understood as meaning all the sequences of DNA necessary for this expression in a microorganism, excluding the structural gene itself of the protoen which is to be cloned, that is to say in addition to the promoter, a termination element if this is necessary and/or its in-phase starting codons, for example.

According to a preferred embodiment of the invention, the above plasmids comprise, at least: one origin of replication in the yeasts, in particular the origin of replication of a 2 μm plasmid of yeast, and one yeast gene which enables selection amongst the yeasts.

The plasmid vectors according to the invention can also comprise elements which enable them to be transferred into bacteria in the case of a "shuttle" plasmid, in particular: an origin of replication in the bacteria, for example in *Escherichia coli*, and genes which code resistance to certain antibiotics, in particular to ampicillin and tetracycline.

The DNA of the 2 μm plasmid carrying the replication site in the yeasts enables plasmid vectors according to the invention to be amplified in a yeast which constitutes, as has been indicated above, the host of choice the genetic recombinations to which the present invention relates.

The interest of the gene ura3+ rests in the fact that it enables selection of transformed microorganisms. After transformation of a strain of the phenotype ura3−, only the microorganisms which have integrated a plasmid vector according to the invention will grow on a minimum medium without uracil. The presence of an origin of replication in the bacteria is warranted since a bacterium, in particular *Escherichia coli*, is used as the intermediate host in the course of the process for construction of the said vectors, as will be described below.

Similarly, the presence of the genes which code a resistance to certain antibiotics, inter alia ampicillin and tetracycline, enables selection of the transformed bacteria in the course of the process for the construction of the plasmid vectors.

Independently of the plasmid vectors described above, the present invention also relates to the microorganisms transformed by the vectors according to the present invention.

Taking into account, on the one hand, that the main use of the invention consists of the preparation of microorganisms capable of direct fermentation of cellobiose and, on the other hand, as has been indicated above, the yeasts and more particularly those belonging to the Saccharomyces genus seem to be the microorganisms most suitable for realization of this aim, the invention protects the yeasts transformed by the said plasmid vectors, and more specifically a transformed strain of *S. cerevisiae*.

Finally, the present invention relates to a process for the production of proteins, in particular β-glucosidase, which consists in fermenting a suitable medium with a microorganism, in particular a yeast, as described above, and isolating the protein obtained.

The present invention also relates to the protein (the β-glucosidase) obtained by carrying out the said process.

The composition of the fermentation media is known to those skilled in the art, in particular in respect of fermentation by *S. cerevisiae*, but in certain cases it will be useful to be able to carry out direct fermentation of cellulose either by using a strain carrying genes which ensure this fermentation, and in particular the gene which codes β-glucosidase according to the invention, or by using various strains as those according to the invention.

The isolation of the β-glucosidase produced can be carried out by any process, after breaking down the cells, if necessary, when the enzyme is not excreted.

The examples below will illustrate other characteristics and advantages of the present invention.

The use of restriction enzymes and ligases is known to those skilled in the art and, in order to facilitate the description, unless indicated otherwise, the enzymes in question will be used in accordance with the manufacturer's instructions. These enzymes are marketed, in particular, by BIOLABS, MILES LABORATORIES INC., and BOEHRINGER.

The attached figures will permit better understanding of certain aspects of the present invention.

On these figures:

FIG. 2 represents a plan of the restriction of plasmid KF4 and

FIG. 3 represents a plan of the restriction of plasmid PR1.

EXAMPLE 1

Figure 1:
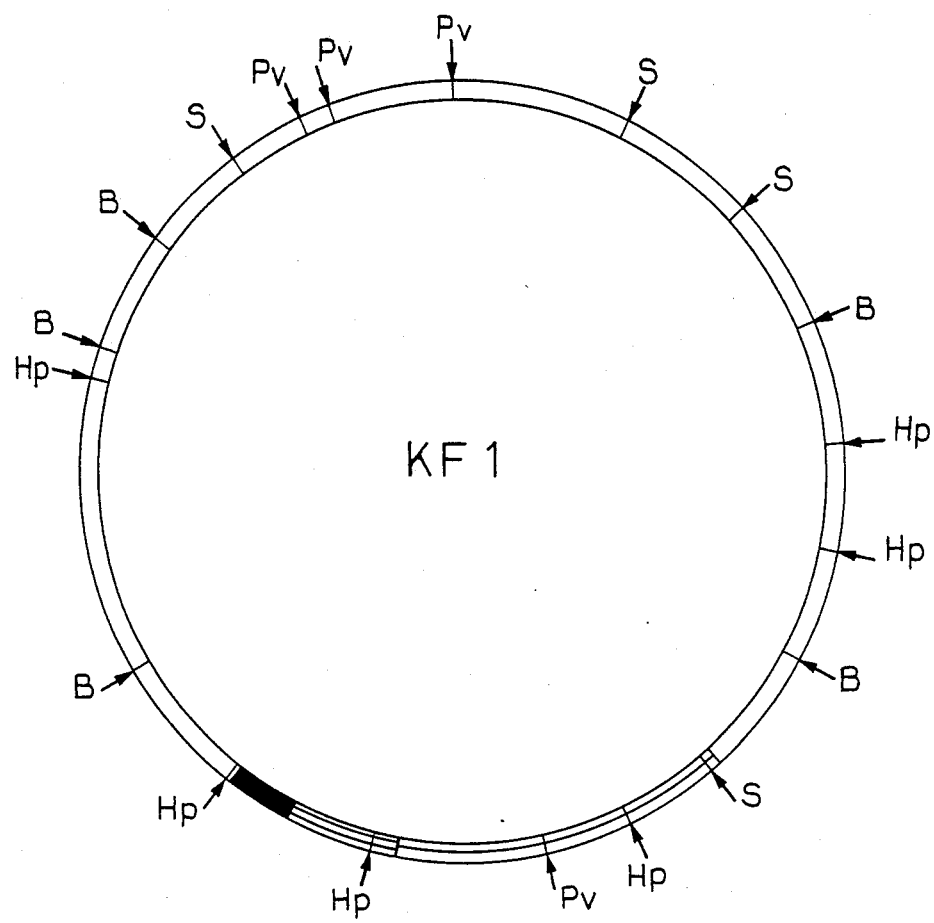
FIG. 1 represents a plan of the restriction of plasmid KF1.

Construction of a gene bank of *Kluyveromyces fragilis* in *Escherichia coli*

A—Donor organism:

The donor organism is a yeast *Kluyveromyces fragilis* (Y610) deposited at the ATCC under No. 12424. This strain produces, in a constituted manner, a β-glucosidase characterized by L. W. FLEMING and J. D. DUERKSEN: Purification and characterization of Yeast β-glucosidase; Journal of Bacteriology (1967) volume 93 pages 135–141.

The DNA of *K. fragilis* is purified by centrifugation in equilibrium in a gradient of CsCl. After the yeast cells have been lysed, a saturated solution of CsCl is added to the lysate in proportions of ⅔ and ⅓ respectively. The mixture is centrifuged at 40,000 rpm for 48 hours in a TFT65 Kontron rotor. The contents of the tube are collected by piercing the bottom of the tube, and the presence of the DNA is shown by the discharge of a very viscous liquid.

After dialysis of the DNA collected against TE (10 mM tris, 1 mM EDTA, pH 7.5) for 24 hours, the DNA is analyzed by agarose gel electrophoresis.

By electrophoresis on a 0.3% gel with the DNA of phage λ (49 kb) as a standard, it is possible to estimate the size of the purified DNA as being at least about 150 kb.

B—Cloning vector:

The cloning vector used is the cosmid PHCG3 described by C. GERBAUD and coworkers: construction of new yeast vectors and cloning of the nif (nitrogen fixation) gene cluster of *Klebsiella pneumoniae* in yeast; Current Genetics (1981) volume 3 pages 173–180. One part of this vector consists of the 2 μm plasmid isolated from *S. cerevisiae* carrying the origin of replication of this plasmid, and a gene of the yeast ura3+.

The other part of this vector is the cosmid pHC79 described by B. HOHN and J. COLLINS: A small cosmid for efficient cloning of large DNA fragments; Gene (1980) volume 10 pages 291–298. The cosmid (CNCMI-686) is a so-called "shuttle" vector, that is to say it can replicate and undergo selection both in *S. cerevisiae* and *E. Coli*, and it is described, in particular, in French Pat. No. 80/18,754.

It also has cosmid properties, which makes cloning of large fragments of DNA possible.

C—Cloning of the gene of β-glucosidase in pHCG3

The DNA of *K. fragilis* is partly digested by the restriction enzyme Sau3A, which enables the chromosomal DNA to be cleaved in a "pseudo-random" manner. After digestion, fragments of 20 to 40 kb are purified by centrifugation in a sucrose gradient (10 to 40%) at a speed of 25,000 rpm for 20 hours in a SW41 Beckman rotor.

Parallel to this, the cosmid pHCG3 is completely digested by the restriction enzyme BamH1.

The purified fragments of the DNA of *K. fragilis* are ligated by the action of T4 DNA-ligase in the presence of ATP and dithiothreitol overnight at 13° C. on the digested cosmid pHCG3. After digestion, the enzymes Sau3A and BamH1 have compatible ends.

D—Preparation of plasmid KF1

The ligation mixture from stage C is then packaged in empty shells of bacteriophage lambda in accordance with the protocol of B. HOHN and J. COLLINS. Cosmids: A type of plasmid gene cloning vector that is packageable in vitro in bacteriophage lambda heads; Proc. Natl. Acad. Sci. U.S.A. (1978) volume 75 No. 9 pages 4242–4246.

The packaging mixture prepared above is used to infect a strain of *E. coli* HB101 which is particularly sensitive to ampicillin and tetracycline. Since the vector used carries bacterial genes resistant to these antibiotics, infected bacteria which are resistant to ampicillin will undergo selection (50 μg/ml). The DNA of *K. fragilis* is inserted at the BamH1 site of the vector, situated in the gene with resistance to tetracycline. In this manner, the bacteria which have received a recombinant plasmid carrying the DNA of *K. fragilis* will be ampicillin-resistant (Amp$^R$) and tetracycline-sensitive (Tc$^S$). 1,800 bacterial clones of Amp$^R$ Tc$^S$ have thus been isolated. In theory, this figure is sufficient to be 98% certain of having cloned a gene donated from *K. fragilis*.

The recombinant plasmid thus prepared is called plasmid KF1. Its structure has subsequently been studied (FIG. 1). Plasmid KF1 consists of a single copy of the vector pHCG3 and an insertion of the DNA of *K. fragilis* of about 35 kb, the total plasmid being 45 kb in size.

E—Investigation of the β-glucosidase activity

The β-glucosidase activity of these 1,800 colonies was investigated by determining the ability to hydrolyse PNPG (p-nitrophenyl β-D-glucoside). Cleavage of the 1-4 β-D-glucoside bond liberates the nitrophenol groupings giving a yellow coloration which can be quantified by the optical density at 400 nm; 1 nM of hydrolysed PNPG produces an increase in the optical densiy of 0.013. The test for the activity is carried out on bacteria which have first been lysed by the action of lysozyme and a mild detergent, Triton X100. A clone from the 1,800 having the required activity was thus isolated. The plasmid DNA isolated from this clone was used to transform the strain HB101. All the resulting transformants produced β-glucosidase. It is thus demonstrated that a fragment of DNA carrying the structural gene of the β-glucosidase of *K. fragilis* has been cloned onto a plasmid, called KF1.

F—Preparation of plasmid KF4

This preparation consists in reducing, by successive sub-cloning, the size of plasmid KF1, and more precisely reducing the size of the DNA fragment of *K. fragilis* inserted into cosmid pHCG3 such that only that part of this fragment which carries the structural gene and the promoting region of the protein to be cloned is preserved.

Each sub-cloning stage consists of deletions in the insertion carried by the plasmid pHCG3. At each stage, after transformation of the strain HB101 of *E. coli*, the β-glucosidase+ transformants carrying a DNA insertion of reduced size are investigated. Plasmid KF1 carrying an insertion of 35 kb has thus been converted, in three successive stages, into plasmid KF4, in which the size of the insertion has been reduced to 3.5 kb (FIG. 2).

EXAMPLE 2

Transformation of a yeast by plasmid KF4

A—Preparation of a transformed strain TYKF4 of *S. cerevisiae*

The plasmids which had undergone selection in *E. coli* were, after purification, transferred into the yeast *S. cerevisiae* by transformation. The receptor strain used for the transformation is the strain OL1, which is double-mutant for the gene ura3. The strain OL1 of *S. cerevisiae* thus transformed constitutes the strain TYKF4.

The plasmids used carry the gene of the yeast ura3+, and after transformation the colonies of prototrophic yeast undergo selection on minimum medium without uracil.

B—Expression of the β-glucosidase in the yeast

The clones which had undergone selection thus received the plasmid and the expression of the gene of β-glucosidase in the transformants TYKF4 of *S. cerevisiae* was studied. The enzymatic analyses were carried out on crude yeast extracts obtained by grinding with glass beads.

The tests were carried out using, on the one hand, PNPG and, on the other hand, cellobiose as substrates. This test makes it possible to determine the level of expression of the gene and whether the β-glucosidase produced was capable of hydrolysing cellobiose.

The results obtained are shown in Table 1. It can be seen that the specific activity of the yeasts transformed with the plasmid KF4 is more than 300 times greater than that observed for the strain of *K. fragilis*.

Taking into consideration: the turnover of β-glucosidase from purified yeast given by H. N. INAMAR and J. C. KAPLAN: $12.1 \times 10^3$ molecules of hydrolysed PNPG per minute per molecule of enzyme; an average molecular weight of β-glucosidase of 300,000 daltons; a specific activity of OL1 transformed by KF4 (TYKF4) of 3,650 nM of hydrolysed PNPG per minute per mg of protein; and a specific activity of OL1 transformed by KF4 (TYKF4) of 600 μg of glucose liberated per minute and per mg of protein. It can be seen that this corresponds to 1,700 nM of hydrolysed celloboise per minute and per mg of protein.

It may be estimated that the β-glucosidase produced in TYKF4 made up about 10% of the total proteins.

This result shows that the gene of β-glucosidase was transcribed from a powerful promoter.

EXAMPLE 3

Sub-cloning of the promoting region

After having determined, from plasmid KF4, the size and transcription sense of the gene of β-glucosidase, it was appropriate, to characterize the promoter region, to sub-clone a fragment covering the gene situated upstream of the Pst1 site of KF4 (FIG. 2). Plasmid KF1 was thus returned to, in order to sub-clone the fragment BamH1-BamH1 of 2.2 kb covering this zone (FIG. 1).

In order to test whether this fragment carries the required promoter, fusion is carried out with the gene lacZ, which produces β-galactosidase. Plasmid pMC2010, constructed by CASADABAN, which carries the lacZ gene of the lactose operon and contains no promoter region or initiation codon, is used. The strains of *E. coli* and *S. cerevisiae* transformed by this plasmid do thus have a phenotype β-galactosidase−. If a DNA fragment carrying a promoter and a codon for the initiation of transcription is inserted into this plasmid, it should then be possible to produce β-galactosidase. The BamH1-BamH1 fragment of 2.2 kb isolated after digestion of KF1 was inserted at the BamH1 site of pMC2010. Plasmid PR1 was thus prepared. After ligation using T4 DNA ligase and transformation of *E. coli*, transformants which produce β-glucosidase were obtained. The recombined plasmid isolated from such transformants was used, after purification, to transform *S. cerevisiae*. It was possible to demonstrate that the resulting transformants produced β-galactosidase (FIG. 3). These results thus clearly demonstrate that the sub-cloned fragment of 2.2 kb certainly carries the promoting region.

TABLE 1

| Plasmid vector | Strain | Specific activity tested on | |
|---|---|---|---|
| | | PNPG | Cellobiose |
| — | OL1 | 1 | 0.22 |
| — | K. fragilis | 7.6 | 2.1 |
| KP4 | TYLF4 | 3636 | 600 |

The specific activity tested on PNPG is expressed in nanomoles hydrolysed/minute/mg of protein.
The specific activity tested on cellobiose is expressed in μg of glucose liberated/minute/mg of protein.

We claim:

1. A strain of Saccharomyces transformed by a plasmid vector for the expression of beta-glucosidase, said plasmid vector comprising the structural gene for beta-glucosidase and expression promoter for that gene, said structural gene and said expression promoter both being obtained from *Kluyveromytes fragilis*.

2. A strain according to claim 1, wherein the Saccharomyces is *Saccharomyces cerevisiae*.

3. A process for the production of beta-glucosidase, which comprises growing a strain of Saccharomyces according to claim 1 in a nutrient medium for Saccharomyces, and isolating the beta-glucosidase produced.

4. A process for the production of beta-glucosidase, which comprises growing a strain of Saccharomyces according to claim 2 in a nutrient medium for Saccharomyces, and isolating the beta-glucosidase produced.

* * * * *